United States Patent
Schlossman et al.

(12)

(10) Patent No.: US 9,072,918 B2
(45) Date of Patent: *Jul. 7, 2015

(54) METHOD OF FORMULATING ZINC OXIDE POWDER BLENDS FOR BALANCED UVA/UVB ATTENUATION

(75) Inventors: David Schlossman, Short Hills, NJ (US); Yun Shao, Belle Mead, NJ (US)

(73) Assignee: Kobo Products, Inc., South Plainfield, NJ (US)

( * ) Notice: Subject to any disclaimer, the term of this patent is extended or adjusted under 35 U.S.C. 154(b) by 1201 days.

This patent is subject to a terminal disclaimer.

(21) Appl. No.: 12/328,631

(22) Filed: Dec. 4, 2008

(65) Prior Publication Data
US 2009/0148481 A1    Jun. 11, 2009

Related U.S. Application Data

(60) Provisional application No. 60/992,711, filed on Dec. 5, 2007.

(51) Int. Cl.
*A61Q 17/04* (2006.01)
*A61K 8/27* (2006.01)
*B82Y 5/00* (2011.01)

(52) U.S. Cl.
CPC . *A61Q 17/04* (2013.01); *A61K 8/27* (2013.01); *A61K 2800/413* (2013.01); *B82Y 5/00* (2013.01)

(58) Field of Classification Search
None
See application file for complete search history.

(56) References Cited

U.S. PATENT DOCUMENTS

| | | | | |
|---|---|---|---|---|
| RE28,626 E | * | 11/1975 | Miyatsuka | 430/87 |
| 7,101,427 B2 | | 9/2006 | Dransfield | |
| 7,220,305 B2 | | 5/2007 | Dransfield | |
| 7,503,970 B2 | | 3/2009 | Dransfield | |
| 8,383,087 B2 | * | 2/2013 | Schlossman et al. | 424/59 |
| 2003/0161795 A1 | * | 8/2003 | Tsuzuki et al. | 424/59 |
| 2006/0222610 A1 | * | 10/2006 | Elliott | 424/63 |

FOREIGN PATENT DOCUMENTS

WO    WO 9011067 A1 * 10/1990

* cited by examiner

*Primary Examiner* — Carlos Azpuru
*Assistant Examiner* — Casey Hagopian
(74) *Attorney, Agent, or Firm* — Handal & Morofsky LLC

(57) ABSTRACT

Disclosed is a composition that comprises an effective proportion of a first metal oxide powder having a primary particle size and a secondary particle size selected for the first metal oxide powder to attenuate UVA and an effective proportion of a second metal oxide powder having a secondary particle size selected for the second metal oxide powder to attenuate UVB. The mean secondary particle size of the first metal oxide powder is greater than the mean secondary particle size of the second metal oxide powder. In one embodiment, the first and the second metal oxide powders are both zinc oxide.

25 Claims, No Drawings

METHOD OF FORMULATING ZINC OXIDE POWDER BLENDS FOR BALANCED UVA/UVB ATTENUATION

The application claims the benefit of U.S. Provisional Patent Application No. 60/992,711 filed on Dec. 5, 2007.

BACKGROUND

The present invention relates to novel zinc oxide powder blends, their production and use and particularly, although not exclusively their use in cosmetics compositions. The invention includes methods of producing the novel zinc oxide powder blends, the zinc oxide powder blends produced, and end-product formulations incorporating the zinc oxide powder blends. Without limitation the invention furthermore includes cosmetic, pharmaceutical and sunscreen formulations, as well as cosmetic and sunscreen formulations all having UV-protective properties attributable to the incorporated zinc oxide blends. The ultraviolet ("UV" herein) region of the electromagnetic spectrum comprises three wavebands, designated UVA from 320 to 400 nm, UVB from 290 to 320 nm and UVC from 200 to 290 nm. The UVA bank can be further divided into UVAI from 320 to 340 nm and UVAII from 340 to 400 nm. The visible portion of the spectrum is generally from about 400 to about 700 nm. Natural sunlight is a potent source of UV radiation. UV radiation may compose about 10 percent of the solar radiation reaching the earth's surface and is well recognized as the cause of serious biological damage to humans and other animals.

Awareness of the risks and prevalence of UV-induced skin cancer and consciousness of the damaging cosmetic effects of ultraviolet radiation have fostered recognition in recent years of the desirability of avoiding or controlling the physiological damage wrought by harmful ultraviolet radiation, especially solar ultraviolet. UVC radiation is generally not problematic as little if any penetrates the atmosphere, but may be hazardous if artificial sources such as germicidal lamps or high or low pressure mercury arc lamps are employed.

In contrast to the UVC waveband which is filtered out, both UVA and UVB radiation reach the earth's surface from the sun and may be harmful. Longer wavelength ultraviolet rays in the UVA region, adjacent the visible spectrum, which reportedly constitute 99% of the UV energy reaching the earth's surface, are considered to be the primary cause of tanning but to cause little burning. However, in the longer term UVA rays are also believed responsible for skin aging, causing blotching, freckling, wrinkling and comparable problems. Ultraviolet radiation in the shorter wavelength UVB region of from 290 to 320 nm, though comprising only about 1% of the UV energy is considered more significant in causing burning. Accordingly, protection against UVB radiation has traditionally been a primary target of sunscreen formulation. More recently, there has been a recognition of the desirability of also protecting against UVA radiation to reduce long term skin deterioration.

More seriously, both the UVA and UVB wavebands may be implicated in skin cancers including dangerous melanomas. Skin cancer is by far the most prevalent of all cancers and the incidence in the US is increasing rapidly. for these and other reasons, consistent use of a topical sunscreen is now strongly recommended and is widespread. In light of this need, the art contains many proposals for sunscreen agents and compositions intended to provide protection from damaging ultraviolet radiation.

Many and diverse UV-protective agents suitable for topical application in creams, sprays, lotions and the like is known and has been used in sunscreens. However, most such agents are organic chemicals that are prone to photodegradation and may cross-react with other components of desirable topical formulations. Furthermore, being absorbable into the skin, organic sunscreens may irritate the skin or cause other dermatological or allergenic problems. The art also contains proposals for broad spectrum UV protection.

For example, Deckner U.S. Pat. No. 5,783,174 describes sunscreen compositions intended to provide broad protection in both the UVA and UVB regions which compositions combine a UVA-absorbing dibenzoylmethane sunscreen with a UVB-absorbing benzylidene camphor sunscreen. This composition is intended to avoid problems of photochemical instability attributable, according to Deckner, to photoinduced interaction between dibenzoylmethane and the widely used UVB absorber octylmethoxy cinnamate.

A more recent demand for both higher SPF ("sun protection factor") values and for broad-spectrum protection, has led manufacturers to combine several different organic chemical ingredients, aggravating potential problems of photo-induced cross reactivity. To overcome this problem, Lapidot, et al. describe in U.S. Pat. No. 6,436,375 a method for microencapsulating at least one of two or more active sunscreen ingredients which are photo-unstable when formulated together. The active ingredients can be selected for UVA and UVB activity and can be encapsulated in separate sol-gel microcapsules. A drawback of Lapidot et al.'s proposal is that even if problems of cross-reactivity and photodegradation can be overcome, which may or may not be the case, Lapidot et al.'s method still requires use of active organic sunscreen agents which may be harmful or irritating when absorbed. Furthermore, use of sol-gel microcapsules adds complexity and expense and may be undesirable in some topical formulations. Such microcapsules may also raise issues of dispersibility and compatibility with other ingredients of end product formulations.

There is accordingly a need for a UV-protective agent having broad spectrum activity against harmful solar radiation and which does not depend upon organic chemicals. In light of the problems with organic materials, the suitability of inorganic materials may be considered. Several commercially useful inorganic UV-protective agents are known, notably titanium dioxide, zinc oxide and iron oxide. Iron oxides, however are usually colored or black and therefore have rather limited use in sunscreen applications. Also, they may not be approved for use as sunscreens by regulatory authorities such as the US FDA.

Thus, considerable difficulties face a formulator or other worker seeking broad spectrum UV-protective agents that will be satisfactory for widespread commercial use in a full range of topical commercial products.

Elsom et al. (WO 90/11067) provide single-species metal oxide sunscreen compositions. Specifically provided are sunscreen compositions containing blends of titanium dioxide powders having a particle size of 1-100 nm.

Likewise, Cowie et al. U.S. Pat. No. 4,927,464 also provides single-species titanium dioxide compositions for absorbing UV radiation. Cowie et al. use acicular titanium dioxide wherein the length of the longest dimension is 10-150 nm and the particles are coated with a mixture of alumina and silica.

Iwaya U.S. Pat. No. 5,032,090 suggests use of a combination of titanium dioxide and zinc oxide in anti-suntan cosmetic compositions to block ultraviolet rays in both the UVB and UVA regions. One drawback of this approach is that titanium dioxide may undesirably whiten or blue the skin in some formulations. Also the use of multiple metal oxides having significant reactivity in many sunscreen systems may complicate the issues a formulator of compositions for human topical application must address. Furthermore, although titanium dioxide is approved by regulatory agencies for many UV-protective applications, it is not approved for use in combination with avobenzone, a popular organic sunscreen agent. In addition, titanium is not naturally present in human and other organisms, and may therefore be an undesired ingredient for some prospective users.

Iwaya U.S. Pat. No. 5,032,090 suggests use of a combination of titanium dioxide and zinc oxide with a primary particle size great than 70 nm to 300 run in anti-suntan cosmetic compositions to block ultraviolet rays in both the UVB and UVA regions. The primary particle size of the zinc oxide claimed is too large to be effective in UVB.

Other formulations of the prior art use single-species zinc oxide compositions for UV absorption. For example, Kobayashi Kose Co. JP 60-231607 provides anti-suntan cosmetics containing 10-30% zinc oxide having a particle diameter of <100 nm.

Mitchell et al. U.S. Pat. No. 5,587,148 discloses sunscreen products intended to absorb both UVA and UVB radiation while providing a clear appearance on the skin. One embodiment of Mitchell et al.'s disclosure employs micronized particles of zinc oxide having a size up to about 0.2 μm and having what are purportedly reduced levels of toxic heavy metals, which are formulated with a liquid carrier into a colorless emulsion. According to Mitchell et al., this formulation "is capable of absorbing a substantial quantity, if not all, of the UV radiation to which the user is exposed." (Column 7, lines 15-17.) However, the Mitchell et al. specification provides little, if any, support for this conclusion. Other distinct embodiments proposed by Mitchell et al. include: use of large crystals of zinc oxide, measuring between about 1-100 microns in diameter; and use of transparent plastic spheres measuring between about 0.01-100 microns in diameter which incorporate a UV-absorbing additive.

Cole et al. U.S. Pat. No. 5,340,567 provides sunscreen products intended for UV absorbance. Cole et al. provide mixed metal oxide compositions containing titanium dioxide having a particle size of less than about 35 nm and zinc oxide having a particle size of less than about 50 nm. The metal oxide particles used by Cole et al. are each of a single substantially uniform size.

A disclosure by inventors herein Yun Shao and David Schlossman, "Effect of Particle Size on Performance of Physical Sunscreen formulas" PCIA conference, Shanghai, China R. P. (1999) ("Shao et al. 1999" hereinafter) and available, at the date of this application, describes some of the effects of size, surface treatment, dispersion vehicle, dispersant and other factors on the UV-protective performance of inorganic sunscreens, notably titanium dioxide and zinc oxide. Shao et al. 1999 emphasize the importance of studying size reduction and the relationship between particle size and performance.

Shao et al. 1999 describe use of dispersions, or "pre-dispersions" of titanium dioxide and zinc oxide, intended for formulation with other ingredients to provide useful end product. Shao et al. 1999 concluded at that time that a high loading of solids in the dispersion were important to size reduction and that other factors should also be considered, including pigment selection, surface treatment, vehicle and dispersant. Titanium dioxide is described as providing excellent protection against UVB along with effective UVA protection at a larger size where scattering may contribute significantly. However, such larger sizes may sacrifice some degree of SPF and transparency.

The protection afforded by zinc oxide is considered by Shao et al. 1999 to vary inversely with particle size. Also, zinc oxide is described as providing efficient UVA protection, often with a low SPF. One difficulty these findings present to the worker seeking to provide a broad-spectrum inorganic UV-protective agent suitable for topical application, is that desired sizes of titanium dioxide particles may cause whitening on the skin, as may be understood from FIG. 5 of Shao 1999. (Nor does Shao et al. 1999 describe an adequate zinc oxide formulation.

Another disclosure of inventors, Yun Shao and David Schlossman herein, namely Discovering an Optimum Micropigment for High UV Shielding and Low Skin Whitening, 23rd IFSCC Congress Orlando 2004 ("Shao et al. 2004" hereinafter) describes studies on the UV attenuation of dispersions of titanium dioxide having a primary particle size ("PPS") as small as 15 nm and of zinc oxide as small as 20 nm which studies include studies of their in vivo SPF efficacy. Shao et al. 2004 conclude that size reduction of titanium dioxide and zinc oxide can remarkably improve the appearance of a sunscreen lotion and can improve the SPF in many cases. However, according to Shao et al. 2004, if the size of the titanium dioxide particles is too small, the energy absorption may shift to UVC wavelengths, weakening the attenuation in the UVA and UVB wavebands. Shao et al. 2004 conclude that zinc oxide could provide an effective SPF at (secondary) particle sizes under 130 nm, but "at the cost of UVA protection".

In this specification, "primary particle size" may be understood to reference an average or mean particle size of the metal oxide as dry powder while "particle size" sometimes referenced herein as "secondary particle size" for greater clarity, can be understood to reference the average mean particle size as it is determined in a dispersion of the metal oxide powder in a liquid.

As may be understood from Shao et al. 2004, secondary particle size may often be more important for ultraviolet protection than is the primary particle size, but the primary particle size of the dry powder is often, but not always, a principal factor in determining the secondary particle size in a liquid dispersion. Some of the data described in Shao et al. 2004 shows that secondary size does not always correlate with primary size. The secondary particle size will usually be substantially greater than the primary particle size, possibly as much as five times greater or even more.

In vivo studies reported in boxes 7-9 of Shao et al. 2004 describe several properties of sunscreens employing the described titanium dioxide and zinc oxide dispersions, including the SPF, the SPF per % of active ingredient and, in box 8, the PFA. "PFA" is a measure of the protection afforded against UVA. Desirable values for PFA may be in the range of from about 4 to about 8. Referring to box 8, which addresses the UV protection of zinc oxide dispersions, no PFAs are reported for the first three test samples, reading down Table 7, which are all described as having relatively smaller (secondary) particles sizes, "PS(nm)", of 110 nm or 130 nm. The last three samples are described as having larger (secondary) particles sizes of 228 nm, or greater, and yield PFAs which are in the target range.

EIsom et al. (WO 90/11067) provide sunscreen compositions which comprise a blend of different particle sizes of titanium dioxide. Preferred compositions comprise 10 to 70% of titanium dioxide having a mean primary particle size of about 15 nm and at least one further grade of titanium dioxide having a mean primary particle size of between about 30 nm and about 50 nm. One drawback of this approach is that titanium dioxide may undesirably whiten or blue the skin in some formulations. The compositions are described as substantially transparent, however, because the refractive index of titanium dioxide is 2.6 they are likely to be too whitening when the objective is to obtain an SPF 25 with a UV balance of 4:1.

"Shao et al. 2004" is here described for the sake of completeness in elucidating the background of the present invention. However, it is to be understood that no admission is made regarding the availability of Shao et al. 2004 as a reference in the United States or any other state or region against the claims of the present application.

Thus notwithstanding the foregoing and other proposals in the art, there is a need for improved UV-protective compositions having properties satisfying the various cosmetic and prophylactic needs of the end user as well as the requirements of a cosmetic formulator who must provide appealing, functional products which can be provided to consumers in a satisfactory and aesthetic condition.

In an earlier filed P.C.T. Patent Application No. PCT/US2006/041417, filed Oct. 23, 2006, we describe a composition which provides an inorganic UV-protective composition which can provide broad-spectrum UV protection, while also being capable of being formulated into end products which have good transparency to visible light on the skin.

Generally, in accordance with the present invention, sunscreen ingredients for cosmetics, suntanning lotion, or the like in both powder and in liquid dispersion form are made from two different sunscreen materials. Each of these two different sunscreen materials is selected for its characteristic of addressing either the UVA or the UVB component of sunlight. In connection with this, it is noted that both of these components will attenuate UVA and UVB, but are, in the context of the multi-mode formulations of the present invention, more effective in addressing either the UVA or the UVB component.

A desirable additional object of the invention is to provide an inorganic UV-protective composition capable of being formulated into dispersions which are non-whitening or induce little whitening at high solids loadings. A still further useful object is to provide dispersions containing the inorganic UV-protective composition that avoid or induce little bluing on pigmented skin.

These and other objects can be achieved by one or more embodiments of the invention described herein.

In one aspect, the invention provides a zinc oxide powder composition for UV-protective use comprising a blend of:

a) an effective proportion of a first zinc oxide powder component having a first particle size selected for the first zinc oxide powder component to attenuate UVA; and b) an effective proportion of a second zinc oxide powder component having a second particle size selected for the second zinc oxide powder component to attenuate UVB;

wherein the mean particle size of the first zinc oxide component is greater than the mean particle size of the second zinc oxide component.

The relative proportions of the first and second zinc oxide components can be adjusted, or selected, to provide a desired balance of UVA versus UVB protection. For example, the proportion by weight of the first component to the second component may be selected to be in the range of from about 1:2 to about 2:1. Some useful embodiments of the invention employ a proportion by weight of the first component to the second component in the range of from about 1:1.4 to about 1:1.

In another aspect, the invention provides a UV-protective composition comprising an effective amount of a first zinc oxide particulate component having a mean primary particle size in the range of from about 30 to about 200 nm and an effective amount of a second zinc oxide particulate component having a mean primary particle size in the range of from about 10 to about 30 nm. As indicated above, "primary particle size" references the size of the dry, untreated powder.

In a further aspect, the invention provides an UV-protective composition comprising a dispersion in a liquid vehicle of an effective amount of a first zinc oxide particulate component having a mean secondary particle size greater than about 180 nm and an effective amount of a second zinc oxide particulate component having a mean secondary particle size less than about 150 nm. As indicated above, the secondary particle size references the size of the particles in the dispersion. Particle sizes referenced herein are as determined by light scattering analysis, as described hereinafter unless otherwise indicated explicitly or by the context.

Suitable dispersions may employ hydrocarbon or other fluids or oils or silicone fluids as liquid vehicles, although aqueous vehicles may also be used. The dispersions are preferably solids-rich. Usefully, the solids-rich zinc oxide dispersions may employ effective, usually small, proportions of chemical dispersing agents, or dispersants, as is known to those skilled in the art. Also the zinc oxide particles may be coated to enhance their dispersibility, as is also known in the art.

Alternatively, the formulator may incorporate the zinc oxide powder blend, in powder form, with other suitable ingredients to prepare a final product. As a further alternative the zinc oxide powder components, rather than being pre-blended may be separately added.

The two zinc oxide components can be supplied for incorporation into the UV-protective product as a particulate or powder blend or may be separately added to one or more other ingredients to provide the UV-protective composition. Some process embodiments of the invention include steps of blending the two or more dry zinc oxide powder ingredients together and adding the blend to other ingredients. Pursuant to the invention it is believed that, in end product formulations, the first and larger zinc oxide component can provide useful UVA protection and the second and smaller zinc oxide component can provide useful UVB protection.

The first zinc oxide powder component can have a mean primary particle size in the range of from about 50 to about 200 nm to provide UVA protection. In one embodiment of the invention the primary particle size of the first zinc oxide component is in the range of from about 60 to about 100 nm.

The second zinc oxide powder component can have a mean primary particle size in the range of from about 10 to about 30 nm to provide UVB protection. In another embodiment of the invention the primary particle size of the second zinc oxide component is about 20 nm.

Our earlier composition contemplated embodiments employing combinations of the mean particle sizes of the first and second components, for example one tranche of zinc oxide particles having a mean size in the range of about 50 to about 200 nm with another tranche of zinc oxide particles having a mean size in the range of about 10 to about 30 nm, for particles of size of from about 60 to about 100 nm of the first component may be combined with particles of size of about 20 nm of the second component.

SUMMARY

In accordance with the present invention, it has been discovered that when it is desired to fabricate blends of zinc oxide intended to provide protection against both UVA and UVB radiation, effectively secondary particle size is of particular importance in achieving the desired attenuation in the UVA range, while primary particle size is relatively unimportant. Conversely, while secondary particle size is determinative in the case of attenuating UVB radiation, primary particle size is desirably kept within certain ranges. Moreover, in accordance with the present invention, the distribution of particle sizes, and more particularly the content of oversize particles (for example, those greater than 280 nm) may be particularly important in preventing whitening.

DETAILED DESCRIPTION

Some embodiments of the invention, and of making and using the invention, as well as the best mode contemplated of carrying out the invention, are described in detail below. The following more detailed description of the invention is intended to be read as a whole with the preceding summary and background descriptions which may also include pertinent description of the invention, the scope of application of the invention or of elements of the invention, as will be apparent to those skilled in the art, in light of this specification when read as a whole.

The present invention provides novel inorganic compositions of particulate, i.e. powdered, UV-protective ingredients that have broad spectrum activity and provide useful absorption and/or scattering in both the UVA and UVB wavebands of the solar energy received at the earth's surface.

In one embodiment, the inventive compositions comprise first and second zinc oxide powder components having particle sizes, or size distributions chosen to selectively attenuate, by absorption, scattering or both absorption and scattering, the UVA and UVB wavebands respectively. For example, the one component may have relatively larger particles to selectively absorb UVA and the other component may have relatively smaller particles to selectively absorb UVB. Desirably, the two zinc oxide powder components can be formulated into compositions, such as dispersions, which are transparent when topically applied, for which purpose relatively small, submicron sized particles may be employed.

UV-protective agents are agents which help or are intended to help protect organisms, especially humans and other susceptible animals, from the harmful effects of UV radiation, notably, without being so limited, solar radiation at the earth's surface. Typically, although not exclusively, such protection is obtained by topical application to the skin and other surfaces of compositions formulated with suitable, protective proportions of one or more UV-protective agents. It will be understood that compositions, including compositions described herein, which effectively protect human skin, may have other useful protective functions e.g. in industrial coatings, plastics or other products.

"UVA" as used herein references the electromagnetic waveband from about 320 nm to about 400 nm and "UVB" references the waveband from about 290 nm to about 320 nm. The first zinc oxide component can be selected to provide an attenuation peak in the UVA waveband, by absorption and/or scattering of the radiation which attenuation peak is useful in preventing the harmful effects of UVA radiation. Comparably, the second zinc oxide component can be selected to provide an attenuation peak in the UVB waveband, by absorption and/or scattering of the radiation which is useful in preventing the harmful effects of UVB radiation. Such a combination of components can provide effective broad-spectrum protection against the UV components of atmospherically filtered solar radiation.

The inventive zinc oxide powder blends are to be understood to include not only dry physical admixtures of the two defined zinc oxide powder components but also other combination these two zinc oxide powder components, for example dispersions of the two components in a liquid vehicle, which dispersions are formed by separate addition of the individual zinc oxide powder components to the liquid vehicle. End products, or intermediate products, which are themselves powder blends, or largely comprise powder blends, can also comprise the individually added or blended zinc oxide components.

The invention provides compositions comprising relatively simple ingredient mixtures that are attractive to a cosmetics formulator to use in preparing formulations for topical application. Such formulations may include, without limitation, sunscreen oils, creams, lotions and the like, and other cosmetic, dermatologic, pharmaceutical or medicament compositions for topical or other use. One object fulfilled by the invention is to provide beneficial UV-protective compositions which avoid presenting new challenges or concerns to a cosmetics formulator. Another is to provide the formulator easy-to-use UV-protective compositions which can readily be incorporated not only in topical sunscreen products to provide protection against acute exposure, but also in other cosmetic products including, without limitation, products such as lipsticks and lip balms, makeups, nail polishes, hair treatments, and so on, to provide everyday protection.

With these objectives in mind, the formulator may be faced with the daunting challenge of assessing not only the individual safety and efficacy of a long list of ingredients under various conditions, but also that of determining whether adverse cross-reactivity or other interactions may occur. For these understandable reasons, the formulator may be reluctant to employ unfamiliar or untried ingredients or combinations of ingredients that do not have a long history of safe and effective use. The compositions of the present invention avoid these problems by providing novel UV-protective compositions which employ active ingredients that are known to be safe and effective and have a long history of satisfactory use in a wide variety of cosmetic and other formulations.

Proportion of Zinc Oxide in Solids Dispersions

The dual component zinc oxide materials of the invention can be dispersed into a suitable lipid, silicone or aqueous liquid vehicle in any desired proportion that will provide a smooth, homogenous dispersion and an effective proportion of zinc oxide for the intended purpose. For example, a proportion of from about 5 to about 90 percent by weight the zinc oxide material, based on the weight of the dispersion, can be employed.

Some useful embodiments of the invention employ a zinc-oxide solids loading, or proportion of at least about 20 percent, desirably at least about 30 percent, by weight, for example a proportion in a range of from about 20 to about 80 percent by weight. Lower proportions containing, for example, up to about 40 percent zinc oxide material, can be useful for direct topical application or other purposes. Higher proportions containing, for example, from about 50 to about 80 percent zinc oxide material, can provide useful "premix" solids-rich dispersions suitable for use by cosmetic, pharmaceutical or other formulators for combining with other ingredients to provide useful consumer or other products, as described herein.

For higher SPF values in the end product, and for other purposes, it may be desirable to use a high proportion of zinc oxide solids in the dispersion, consistent with providing a stable, homogenous, dispersion that has enough fluidity for processing. In other words, a high loading of solids is generally desirable for product efficacy, but a loading which is too high may cause processing difficulties or yield a poor quality product. Some useful embodiments of the invention employ more-or-less the highest loading of zinc oxide which can be obtained in a smooth dispersion that has sufficient fluidity for processing. Such products may have a solids content in the range of from about 40 to about 75 percent by weight of the dispersion.

A high proportion of solids in the liquid dispersion medium can be beneficial to the objectives of the invention, as is described herein. For example, during milling of the dispersion, when milling is employed, a high proportion of solid particles can enhance attrition, causing more collisions between particles and converting more of the input energy to size reduction. In addition, a high proportion of solids provides the resultant dispersion with a high viscosity which may be advantageous, for example helping to control re-agglomeration.

Proportions of Zinc Oxide in End Products

Any proportion of zinc oxide powder or powder blend, may be employed in end product formulations that is effective for one or more of the purposes described herein may be employed.

For example a desirable proportion of the two-component zinc oxide material of the invention may comprise from about 0.1 percent to about 50 percent by weight of the end product. Desirably, the proportion is from about 1 to about 40 percent by weight. Higher proportions in either of these ranges, for example from about 2 to about 30 percent can be useful in a variety of preparations that function primarily as sunscreens and lower proportions, for example from about 0.1 to about 5 percent by weight can be useful in preparations having other utilities where a lower level of UV protection is considered useful, e.g. everyday cosmetics.

The invention includes embodiments of sunscreen or UV-protective compositions intended for topical application to skin, nail or hair comprising from about 2 to about 25 percent by weight zinc oxide material. One such embodiment, or group of embodiments, has a proportion of zinc oxide material of from about 5 to about 10 percent by weight of the end product. Another employs from about 10 to about 15 percent by weight of zinc oxide material.

Preparation of Dispersions and Formulation into End Products

Various methods can be employed to prepare the zinc oxide materials of the invention for delivery in a useful form to a cosmetics, pharmaceutical or other formulator, for formulation into UV-protective products useful to consumers or other end users.

For example, a specialist vendor, or other supplier may prepare a solids-rich dispersion of the zinc oxide powder blend in a liquid vehicle for use by a formulator, or possibly for direct topical application. The liquid vehicle in such solids-rich dispersions may comprise a suitable oil, a hydrocarbon, a silicone fluid, an aqueous medium or other useful and suitable liquid medium.

The solids-rich zinc oxide dispersions in oil can for example be prepared by first mixing two or more dry powdered commercially available zinc oxide powder components of desired size with the liquid vehicle, in a homogenizer or blender to break up agglomerates. Suitable zinc oxide materials are available inter alia from Tayca Corp. and Advanced Nanotechnology Ltd., (Welshpool, Western Australia). Suitable oils include, for example, isononyl isononanoate, octyl dodecyl neopentanoate and many other oils as are known in the cosmetics, pharmaceutical and other relevant arts. Other suitable liquids include aqueous vehicles and silicone fluids.

The product of mixing, using a high sheer mixer or homogenizer, may be satisfactory, without milling.

However, if desired the dispersion product of the homogenizing or blending process can then be processed in a ball mill or the like to reduce agglomerates and aggregates into smaller particles, continuing milling until a smooth, homogenous dispersion is obtained. The zinc oxide powder components can be added as a powder blend or may be added separately to the liquid vehicle, while mixing, and/or agitating.

Surface Treatments or Coatings

Usefully, the zinc oxide powder materials may be surface treated to enhance the quality of the dispersion, increase the proportion of solids that can be successfully loaded into the liquid vehicle and thus help provide the end product with a small particle size. If desired, the surface treatment can be selected according to the nature of the intended end product, some options for which are described below.

One or more surface treatment materials, for example a coating agent, is or are blended together with the zinc oxide powder, employing a small quantity of solvent or dispersion vehicle, if needed for workability. This mixture is then heated, while blending or agitating, to a suitable temperature, e.g. from about 110 to about 130° C. and for an appropriate time e.g. from about 2 to about 4 hours or other suitable time period in the range of from about 30 minutes to 24 hours to effect the surface treatment and any associated chemical reaction such as surface bonding, polymerization or cross-reaction. The treated zinc oxide material is mixed into a suitable cosmetic or other liquid vehicle and milled to a fine particle size, for example to the finest size routinely obtainable.

Some suitable surface treatments are described in Shao et al. 1999 and include: use of metal soaps, titanates such as isopropyl titanium triisostearate or lecithin or the like to provide the treated zinc oxide particles with lipophilic properties; use of various silicone materials such as methicone, dimethicone and multifunctional reactive silanes, e.g. triethoxy caprylylsilane to provide hydrophobic properties; and use of reactive fluorinated compounds such as fluoroalcohol phosphate to provide both lipophobic and hydrophobic properties.

Other materials can be used for surface coating as known to those skilled in the art, or as becomes known as the art develops. Some such useful coatings, coated zinc oxide materials and formulations embodying same are disclosed in U.S. Patent Publications Nos.: 2005/0037041 "Duplex coated color lake and other powders, their preparation and cosmetic and other uses"; U.S. 2004/0234613 "Hybrid coated cosmetic powders and methods of making and using same"; and U.S. 2003/0161805 "Organosilicon treated cosmetic powders, their production and use"; each of which patent publications has at least one inventor in common with the present application and are commonly owned with the present application at the date hereof. The disclosure of each of said patent publications is hereby incorporated herein by this specific reference thereto.

Dispersing Agent

With advantage a dispersing agent or dispersant can be employed in the dispersion to improve dispersion quality, for example PEG 10 dimethicone or acrylates/ethylhexyl acrylate/dimethicone methylacrylate copolymer, or any other suitable dispersing agent as is known or becomes known in the art, some examples of which include polymeric acid amines formed by condensation of a polymeric acid with an amine, for example as described in U.S. Pat. No. 4,349,389 at col. 5, 11. 5-35, the disclosure of which is hereby incorporated herein by reference thereto. The polymeric acid can be a polyester derived from a suitable hydroxy organic acid, for example hydroxystearic acid. The amine employed can be a lower alkylamine, di- or tri-lower alkylamine, or a polyamine for example methylamine, diethylamine, triethylamine, dimethylaminopropylamine, ethylenediame, triethylenetetramine, quanidine or a derivative thereof. Useful dispersing agents include SOLSPERSE (trademark), SOLSPERSE 9000, SOLSPERSE 3000 dispersing agents available from ICI Americas Inc., Wilmington, Del. and the dispersing agents disclosed in U.S. Pat. Nos. 4,349,389, 3,778,287 and 4,157,266. Many other suitable dispersing agents will be known to those skilled in the art, or will become known as the art evolves.

For example, one useful embodiment of the invention employs a polyhydroxystearic acid as a dispersant for an oil, ester or hydrocarbon vehicle. Another embodiment employs castor oil phosphate as a dispersant for such vehicles. For silicone-based dispersions, in silicone fluids, a further embodiment of the invention employs a silicone polyether, for example PEG-IO dimethicone as a dispersant.

Dispersion Analysis

With advantage, the viscosity and particle size of the resultant dispersion are then determined. Viscosity can be measured using a Brookfield RVT viscometer, or other suitable instrument, after incubating samples at 25° C. for 24 hours. Particle size can be measured by any suitable method. One useful particle size measurement employs a light scattering analyzer, for example a NICOMP 370 photo-correlation particle analyzer. Secondary particle sizes described herein are to be understood to be as determined by such an instrument. Primary particle sizes are as determined and specified by a product supplier. If desired, the primary particle size can be determined or verified by such light scattering analytic methods. As is known in the art, primary particle size can be measured from a SEM (scanning electron micrograph) picture or calculated from the specific surface area.

The formulator, or other party can mix the solids-rich zinc oxide dispersion, produced by the above or other suitable methods, with other ingredients to provide a desired cosmetic, pharmaceutical or other product for topical application. Other suitable ingredients include cosmetic or pharmaceutical vehicles, pharmaceutically or cosmetically active ingredients, excipients, additives, colorants, pigments, perfumes, water and the like, as is known, or becomes known, or apparent in the respective art. Blending, grinding, milling, mixing, heating, agitation, homogenization and other techniques may be employed, as will be understood by these skilled in the art, to combine and process the various ingredients into useful end products.

If desired, and with advantage, in vivo tests can be performed on the sunscreen compositions produced, to determine in vivo values of SPF, optionally using a US FDA, or other suitable protocol. Such in vivo tests can also be used to determine appearance, spreadability, aroma, and other aesthetic qualities, if desired.

In another embodiment of this aspect of the invention, the zinc oxide powder blend, or the components thereof is, or are, admixed with other powder ingredients, for example pigments, fillers and so on, to provide a powdered end product, for example make up.

Supplemental Organic Sunscreen Agent

The invention also provides a UV-protective composition comprising the dual-component zinc oxide material of the invention in combination with an organic sunscreen agent or agents. Usefully, the organic sunscreen agent can be selected to provide protection against UVB radiation, supplementing that provided by the inventive zinc oxide material. Any desired organic UV-protective agent may be employed, as known, or that becomes known, to those skilled in the art, provided it is compatible with zinc oxide and other ingredients employed in the end product.

One example of a suitable organic UV-protective agent that may be employed is octylmethoxy cinnamate (or 2-ethylhexyl p-methoxycinnamate), commonly abbreviated as "OMC". Others include p-aminobenzoic acid, various benzophenones, oxybenzone, avobenzone, salicylates, various other cinnamates and such organic sunscreen or UV-protective agents as are described in Gildenberg U.S. Pat. No. 6,217,852 and in the patents and other publications referenced in Gildenberg. The disclosure of each one of said patents and other publications is hereby incorporated herein by this specific reference thereto.

Some examples of other organic UV-protective agents that can be employed include octyl salicylate, octocrylene, oxybenzone, 2-ethylhexyl $N_5N$-dimethylaminobenzoate, p-aminobenzoic acid, 2-phenyl-benzamidazole-5-sulfonic acid, homomethyl salicylate, avobenzone (e.g., Parsol 1789), DEA p-methoxycirmamate, octylmethoxy cinnamate, 4/4'-methoxy-t-butyldibenzoylmethane, 4-isopropyldibenzoylmethane, 3-(4-methylbenzylidene) camphor, 3-benzylidene camphor, 4-N,N-dimethylaminobenzoic acid ester with 2,4-dihydroxybenzophenone, 4-$N_5N$-dimethylaminobenzoic acid ester with 2-hydroxy-4-(2-hydroxyethoxy)benzophenone, 4-N,N-dimethylaminobenzoic acid ester with 4-hydroxydibenzoyl-methane, 4-$N_5N$-dimethylaminobenzoic acid ester with 4-(2-hydroxyethoxy)dibenzoylmethane, 4-$N_5N$-di(2-ethylhexyl)-aminobenzoic acid ester with 2,4-dihydroxybenzophenone, 4-N,N-di(2-ethylhexyl)aminobenzoic acid ester with 4-hydroxydibenzoylmethane, 4-N,N-di (2-ethylhexyl)aminobenzoic acid ester with 4-(2-hydroxyethoxy)dibenzoylmethane, 4-$N_5N$-(2-ethylhexyl)methylaminobenzoic acid ester with 2,4-dihydroxybenzophenone, 4-$N_5N$-(2-hydroxyethoxy) benzophenone, 4-N,N-(2-ethylhexyl)methylaminobenzoic acid ester with 4-hydroxydibenzoylmethane, 4-N,N-(2-ethylhexyl)methylaminobenzoic acid ester with 4-(2-hydroxyethoxy)dibenzoylmethane and mixtures of any two or more of the foregoing organic UV-protective agents.

Any suitable proportion of the organic sunscreen agent can be employed. For example, the quantity, by weight may be somewhat less than the quantity of the inventive zinc oxide material employed, for example, from about 0.1 to about 2 parts organic agent, or agents, per part of zinc oxide material referring to the combined weight of organic agents if more than one is employed. Some useful embodiments of the invention employ from about 0.5 to about 1.2 parts organic agent, or agents, per part of zinc oxide material, one embodiment of which employs about 0.8 parts organic agent, or agents, per part of zinc oxide material.

Benefits

The novel dual-component zinc oxide powder materials of the present invention, compositions formulated from the dual zinc oxide powders and the related methods described herein, provide a flexible, biocompatible solution to many ultraviolet protection problems. Cosmetic, dermatological, pharmaceutical, veterinary and other formulators are provided with a novel means of affording both UVA and UVB protection with good transparency, biocompatibility and stability, in sunscreens and other products.

The invention provides a simple inorganic composition, or ingredients therefor, useful embodiments of which have good broad-spectrum ultraviolet efficacy, good SPF (sun protection factor) and PFA (protection factor UVA) which is easy to use, attractive to a cosmetics formulator who must consider physical and chemical properties and interactions of a multiplicity of ingredients. Useful embodiments of the invention also provide good transparency enabling end products that provide good protection against sunlight, are non-allergenic and suitable for extended daily wear and which are attractive to a wide range of users by virtue of their freedom from whitening or bluing.

The provision, by means of the invention, of broad spectrum UV protection using zinc oxide alone, is chemically and biochemically advantageous. The properties of zinc oxide are well understood. The complications of using multiple, chemically diverse components can be avoided. If it is desired to employ an organic sunscreen agent for supplemental UVA protection, the use of a single chemical entity for primary broad spectrum protection limits potential interactivity problems.

The various proportions of ingredients described herein are to be understood to be by weight based on the weight of the relevant composition comprising the ingredient in question, unless the context indicates otherwise.

Products were prepared utilizing zinc oxide of various size, which were treated, by methods known to one of skill in the art, with isopropyl titanium triisostearate or triethoxycaprylylsilane crosspolymer for easy dispersion. The treated zinc oxide was dispersed in isononyl isononanoate using a convention media mill, such as that made by Premier or Netzsch. Alternately, C12-C15 alkyl benzoate may be used as an effective substitute for isononyl isononanoate. the mixture was then milled to the desired size in a manner known to one of skill in the art.

The resultant zinc oxide dispersions were used to make a water in oil sunscreen lotion, as more fully appears below. SPF (protection against UVB) and PFA (protection against UVA) were tested in-vivo on three panelists. To determine PFA, the PPD (persistent pigment darkening) method was used. Particle size in the dispersion was measured using a NICOMp C370 photo correlation size analyzer, Mean size of intensity weighted distribution is given below. Primary particle size of zinc oxide is calculated from their BET specific surface area.

It is noted that the component referred to as providing UVA protection also provides some UVB protection and vice versa, and that such reference is to the primary function.

Water in oil sunscreen formulas were prepared to investigate the effect of particle size on PFA, which, as noted above, measures effectiveness in protecting against UVA. Table 1 illustrates the composition, by weight percent, of Formula 1, results for which are reported in Table 2.

TABLE 1

| Phase | W/W % | INCI NAME |
|---|---|---|
| 1 | 3.00 | Cetyl Dimethicone |
|   | 7.50 | Cyclomethicone |
|   | 6.00 | Isononyl Isononanoate |
|   | 0.50 | Methyl Glucose Sesquistearate |
|   | 2.00 | Dioctyl Malate |
|   | 5.00 | Polyglyceryl-4 Isostearate (and) Cetyl Dimethicone Copolyol (and) Hexyl Laurate (ABIL ® WEO9 available from DeGussa) |
| 2 | 21.33 | Zinc Oxide dispersion in Isononyl Isononanoate |
| 3 | 51.07 | Water |
|   | 0.50 | Sodium Chloride |
|   | 2.50 | PEG150/Decyl Alcohol/Smdi Copolymer (Aculyn 44 available from Rohm & Haas) |
|   | 0.60 | Phenoxyethanol (and) parabens (Phenonip ® available from Nipa) |
|   | 100 |   |

Formula 1 was prepared by mixing the Phase 1 ingredients, namely cetyl dimethicone, cyclomethicone, isononyl isononanoate, methyl glucose sesquistearate, dioctyl malate, and polyglyceryl-4 isostearate, cetyl dimethicone and hexyl laurate, using a propeller mixer. Mixing is done until the mixture exhibits uniformity. Mixing may be carried out at room temperature or, optionally, heated to a temperature of 70-80° C. The zinc oxide dispersion of Phase 2 is then added to the contents of the propeller mixer to complete the "oil" phase.

The dispersion is made using a conventional method.

In a separate propeller mixer, the Phase 3 ingredients, water, sodium chloride, peg-150/decyl alcohol/smdi copolymer, Phenonip®, are mixed at a temperature between 70° C. and 80° C., until the mixture is uniform, thus forming the water phase. Phase 3 is then slowly poured into the mixture of Phase 1 and Phase 2, and mixing is continued until uniformity is achieved. Overmixing is not a problem and mixing may thus be continued until uniformity stabilizes. The resulting mixture is then homogenized at 3000 rpm in a conventional homogenizer for 10 minutes at 70-80° C. The finished mixture is then allowed to cool to room temperature.

TABLE 2

| | Formula | | | | |
|---|---|---|---|---|---|
| | 1 | 2 | 3 | 4 | 5 |
| PPS (nm) | ~100 | 15-35 | 60 | 20 | 20 |
| PS in disp. (nm) | 263 | 228 | 163 | 166 | 130 |
| Active (%) | 16 | 14.97 | 14.97 | 14.97 | 13.80 |
| SPF | 12.6 | 14 | 20.4 | 17.4 | 25.4 |
| SPF/Active % | 0.79 | 0.93 | 1.36 | 1.16 | 1.84 |
| PFA | 5.83 | 7.50 | 7.58 | 8.17 | 4.75 |
| PFA/Active % | 0.46 | 0.50 | 0.51 | 0.54 | 0.34 |
| SPF/PFA | 2.2/1 | 1.9/1 | 2.7/1 | 2.1/1 | 5.4/1 |

In Table 2, the size of primary particles in manometers is reported as "PPS". "PS" refers to secondary particle size, or the particle size of aggregates in the dispersion. "Active (%)" refers to the percentage by weight of the active ingredient, namely the zinc oxide. "PFA" refers to UVA protection.

Formulae 2-5 were prepared in the same manner as a Formula 1, except for the use of zinc oxide having the primary particle size and the secondary particle size indicated in Table 2, and except for the adjustment of the amount of isononyl isononanoate. More particularly, the adjustment of the amount of isononyl isononanoate was made to compensate for the change in percent actives. For example, in Formula 2, the amount of zinc oxide is reduced by 1.03 parts. Accordingly, the amount of isononyl isononanoate was increased by 1.03 parts to result in a product having the reported percent of active material.

From the above, it can be concluded that the smaller the reported size in dispersion, the more effective ZnO is in protecting against UVB. At a size of 130 nm or smaller, ZnO can be a very effective UVB sunscreen. It also appears that it is largely the aggregate size, rather than the primary particle size, that has a decisive influence on SPF score.

For UVA protection, there is an optimal size range of secondary particle sizes, which was found to include 160-230 nm and is believed to range between 150 nm and 250 nm. When size is larger, the ZnO is not fully utilized for absorption, as particles located on the outside of the large aggregate shield inside particles from radiation. When the size is smaller, the effective absorption range narrows.

It also appears from the above results that optimal sizes for UVA and UVB attenuation for zinc oxide are different. In order to formulate for a balanced UV protection, a combination of different sizes appears desirable. Thus, a zinc oxide dispersion with a secondary particle size of 130 nm will provide excellent UVB protection. Zinc oxide dispersions with much larger size particles were used to provide UVA protection, in a number of formulations tested, as detailed in Table 3.

TABLE 3

|  |  | Formula | | |
| --- | --- | --- | --- | --- |
|  |  | 6 | 7 | 8 |
| ZnO for UVB Attenuation | PPS (nm) |  | 20 |  |
|  | PS (nm) |  | 130 |  |
|  | % | 12 | 10 | 10 |
| ZnO for UVA Attenuation | PPS (nm) |  | 60 | 15-35 |
|  | PS (nm) | 250 | 193 | 220 |
|  | — | 10 | 10 | 12 |
|  | SPF | 31.4 | 30 | 30.7 |
|  | PFA | 11.6 | 8.7 | 9.3 |
|  | FDA rating | High | High | High |

The water in oil sunscreen formulations designated Formulae 6-8 were prepared using the method described above in connection with the preparation of Formula 1. Again, to the extent that the percentage of zinc oxide has been reduced from 16%, the amount of isononyl isononanoate has been increased by the same weight. In Formulae 6-8, the UVB attenuating zinc oxide with a primary particle size of 20 nm was obtained from a dispersion sold by Kobo under its catalog number TNP5OZSI. In Formula 6, the UVA attenuating zinc oxide was obtained by using a dispersion sold by Kobo under its catalog number TNC65SZ5. In Formula 7, the UVA attenuating zinc oxide was obtained by using a dispersion sold by Kobo under its catalog number TNP50FZS. In Formula 8, the UVA attenuating zinc oxide was obtained by using a dispersion sold by Kobo under its catalog number INH73MZ.

All of the above formulae have SPF of 30 or higher and an excellent PA, indicating excellent broad-spectrum protection. Formula 6 used sizes at two extremes, and the results met the standard of 3/1 SPF/PFA ratio. Accordingly it is believed that high balanced UV protection can be achieved with a blend of ZnO with sizes at two extremes.

The UV attention of zinc oxide depends more on its aggregate size than the primary size. At very small size, it can be an effective SPF provider. When the particle size is in the range of about 165-220 nm, it is very effective against UVA.

In accordance with the invention, it has been learned that the component of zinc oxide useful for attenuating UVA radiation may be fabricated with zinc oxide particles having a mean primary particle size less than 120 nm. The dispersion is made to result in a secondary mean particle size of 150 to 250 nm, preferably 160 to 240 nm. However, secondary mean particle sizes of 140 to 260 nm will work well and functional results can be obtained with secondary mean particle sizes of 120-280 nm.

It is noted that the above specifications apply to zinc oxide particulates currently available on the market. Other materials having different, for example, more narrow, particle size distributions may enable equivalency outside these ranges.

Secondary particle sizes for particles intended to protect against UVA radiation need only be less than 120 nm in size, as such smaller particles may be aggregated during the dispersion manufacturing process to be in the above specified ranges.

Dispersions incorporating mixtures of zinc oxide particles meant to attenuate UVA radiation should be formulated to have 30% or more of the above particles for an SPF of 30 and a ratio of SPF to PFA of 3:1. For similar results finished products should have secondary particle size zinc oxide concentrations as specified above in the range of 8% by weight.

However, dispersions having 10% or greater UVA attenuating zinc particles may be usefully employed. Likewise, finished products having 2% or more UVA attenuating zinc oxide with secondary particles sizes as specified above will also find useful employment.

The component of zinc oxide useful for attenuating UVB radiation may be fabricated with zinc oxide particles having a mean primary particle size less than 55 nm, preferably less than 35 nm. However primary particle sizes less than 75 nm will yield useful results.

Secondary particle sizes are preferably less than 140 nm, and more preferably less than 130 nm, although mean particle sizes in the 50-150 nm range will provide functional results.

It is noted again that the above specifications apply to zinc oxide particulates currently available on the market. Other materials having different, for example, more narrow, particle size distributions may enable equivalency outside these ranges.

Dispersions incorporating mixtures of zinc oxide particles should be formulated to have 30% or more of the above particles meant to attenuate UVB radiation for an SPF of 30 and a ratio of SPF to PFA of 3:1. For similar results finished products should have secondary particle size zinc oxide concentrations as specified above in the range of 8% by weight.

However, dispersions having 10% or greater UVB attenuating zinc particles may be usefully employed. Likewise, finished products having 2% or more UVB attenuating zinc oxide with secondary particles sizes as specified above will also find useful employment.

As alluded to above, the mean secondary particle sizes are determined by measuring using a photon correlation particle size analyzer, also known as a dynamic light scattering particle size analyzer, such as that made by Particle Size Systems of Santa Barbara, Calif.

With respect to primary particle size measurements, the same are specified using sizes determined using the BET surface area calculation method.

Dispersions may be prepared by incorporating zinc oxide particles into suitable carriers and milling using conventional techniques of UVA attenuating zinc oxide has the desired secondary particle size to make a first dispersion. The dispersions or compositions incorporating such dispersions may also include at least one biocompatible excipient (e.g., buffer (neutralizer or pH adjusters), emulsifier, surfactant, diluent, adjuvant, preservative, and/or electrolyte).

The UVB attenuation particles are then incorporated into a carrier and milled until the desired secondary particle size is obtained to make a second dispersion.

The first and second dispersions are then combined.

The entire disclosure of each and every United States patent and patent application, each foreign and international patent publication, of each other publication and of each unpublished patent application that is referenced in this specification or elsewhere in this patent application, is hereby incorporated herein, in its entirety, by the respective specific reference that has been made thereto.

While illustrative embodiments have been described above, it is, of course, understood that various modifications will be apparent to those of ordinary skill in the art. Many such modifications are contemplated as being within the spirit or scope of the appended claims.

What is claimed is:

1. A composition comprising:
an effective proportion of a first Zinc oxide powder having a primary particle size and a secondary particle size selected for the first Zinc oxide powder to attenuate UVA; and
an effective proportion of a second Zinc oxide powder having a secondary particle size selected for the second Zinc oxide powder to attenuate UVB;
wherein the mean secondary particle size for the first Zinc oxide is about 150 nm to about 260 nm and the mean secondary particle size for the second Zinc oxide is about 130 nm or smaller.

2. The composition of claim 1 wherein the primary particle size of the first Zinc oxide is about 100 nm or smaller and a primary particle size of the second Zinc oxide is about 10 nm to about 30 nm.

3. The composition of claim 1 wherein the mean secondary particle size for the first Zinc oxide is about 160 nm to about 260 nm and the mean secondary particle size for the second Zinc oxide is in the range of about 120 nm to about 130 nm.

4. The composition of claim 3 wherein the first and second Zinc oxide powders are separately formulated into a dispersion that are thereafter blended together.

5. The composition of claim 1 included in a sunscreen composition.

6. The composition of claim 5 wherein the sunscreen composition has an SPF of at least about 25.

7. The composition of claim 6 wherein the SPF is about 30.

8. The composition of claim 6 wherein the sunscreen composition has a PFA of at least about 8.

9. The composition of claim 5 wherein the sunscreen composition has a SPF:PFA ratio of about 3.5:1 or less.

10. A dispersion comprising:
an effective proportion of a first Zinc oxide powder having a primary particle size and a secondary particle size selected for the first Zinc oxide powder to attenuate UVA;
an effective proportion of a second Zinc oxide powder having a secondary particle size selected for the second Zinc oxide powder to attenuate UVB, and
a dispersing agent;
wherein a mean secondary particle size of the firs Zinc oxide powder is greater than a mean secondary particle size of the second Zinc oxide powder, wherein the mean secondary particle size for the first Zinc oxide is about 150 nm to about 260 nm and the mean secondary particle size for the second Zinc oxide is about 130 nm or smaller.

11. The dispersion of claim 10 wherein the first and second Zinc oxide powders are separately dispersed and then blended together.

12. The dispersion of claim 10 wherein the mean secondary particle size for the first Zinc oxide is about 150 nm to about 250 nm and the mean secondary particle size for the second Zinc oxide is about 130 nm or smaller.

13. The dispersion of claim 10 wherein the primary particles size of the first zinc oxide is about 30 nm to about 200 nm and a primary particle size of the second zinc oxide is about 30 nm or smaller.

14. The dispersion of claim 10 included in a sunscreen composition.

15. The dispersion of claim 14 wherein the sunscreen composition has an SPF of at least about 25.

16. The dispersion of claim 15 wherein the SPF is about 30.

17. The dispersion of claim 15 wherein the sunscreen composition has a PFA of at least about 8.

18. The dispersion of claim 14 wherein the sunscreen composition has a SPF:PFA ratio of about 3.5:1 or less.

19. A cosmetic composition comprising:
an effective proportion of a first Zinc oxide powder having a primary particle size and a secondary particle size selected for the first Zinc oxide powder to attenuate UVA;
an effective proportion of a second Zinc oxide powder having a secondary particle size selected for the second Zinc oxide powder to attenuate UVB; and
a biocompatible excipient;
wherein a mean secondary particle size of the first Zinc oxide powder is greater than a mean secondary particle size of the second Zinc oxide powder, wherein the mean secondary particle size for the first Zinc oxide is about 150 nm to about 260 nm and the mean secondary particle size for the second Zinc oxide is about 130 nm or smaller.

20. The cosmetic composition of claim 19 wherein the primary particle size of the first Zinc oxide is in the range of about 20 nm to about 60 nm and a primary particle size of the second Zinc oxide is about 20 nm.

21. The cosmetic composition of claim 19 having an SPF of at least about 25.

22. The cosmetic composition of claim 21 wherein the SPF is about 30.

23. The cosmetic composition of claim 21 having a PFA of at least about 8.

24. The cosmetic composition of claim 19 having a SPF:PFA ratio of about 3.5:1 or less.

25. The cosmetic composition according to claim 20 further comprising organic sunscreen agents or UV protective agents.

* * * * *